US009125623B2

(12) United States Patent
Watanabe et al.

(10) Patent No.: US 9,125,623 B2
(45) Date of Patent: Sep. 8, 2015

(54) RADIOGRAPHIC IMAGING APPARATUS, CONTROL METHOD THEREFOR, AND STORAGE MEDIUM HAVING STORED PROGRAM

(71) Applicant: CANON KABUSHIKI KAISHA, Tokyo (JP)

(72) Inventors: Kazuhiro Watanabe, Tokyo (JP); Sakiko Yamaguchi, Tokyo (JP); Kotaro Izumiya, Kawasaki (JP); Takeshi Nakata, Kawasaki (JP); Wataru Kaku, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 199 days.

(21) Appl. No.: 13/862,778

(22) Filed: Apr. 15, 2013

(65) Prior Publication Data

US 2013/0272502 A1    Oct. 17, 2013

(30) Foreign Application Priority Data

Apr. 17, 2012   (JP) ................................. 2012-093983

(51) Int. Cl.
*A61B 6/00* (2006.01)
*H05G 1/26* (2006.01)

(52) U.S. Cl.
CPC ............. *A61B 6/5235* (2013.01); *A61B 6/4283* (2013.01); *A61B 6/4405* (2013.01); *A61B 6/4411* (2013.01); *A61B 6/4452* (2013.01); *A61B 6/5211* (2013.01); *A61B 6/5229* (2013.01); *A61B 6/547* (2013.01); *H05G 1/26* (2013.01)

(58) Field of Classification Search
CPC .. A61B 6/4405; A61B 6/4411; A61B 6/4452; A61B 6/547
USPC .......... 378/189, 196, 197, 198, 205, 206, 207
See application file for complete search history.

(56) References Cited

U.S. PATENT DOCUMENTS

| 6,036,362 | A  | * | 3/2000 | Schmitt ........................ 378/206 |
| 6,227,704 | B1 | * | 5/2001 | Bani-Hashemi et al. ..... 378/206 |
| 6,260,999 | B1 | * | 7/2001 | Wofford et al. ............... 378/205 |
| 6,305,842 | B1 | * | 10/2001 | Kunert .......................... 378/206 |
| 6,322,249 | B1 | * | 11/2001 | Wofford et al. ............... 378/205 |
| 6,447,164 | B1 | * | 9/2002 | Polkus .......................... 378/206 |
| 6,463,121 | B1 | * | 10/2002 | Milnes .......................... 378/62 |

(Continued)

FOREIGN PATENT DOCUMENTS

| JP | H09-66116 A | 3/1997 |
| JP | 2000-135212 A | 5/2000 |
| JP | 2009-100948 A | 5/2009 |

*Primary Examiner* — Allen C. Ho
(74) *Attorney, Agent, or Firm* — Carter, DeLuca, Farrell & Schmidt, LLP

(57) ABSTRACT

A radiographic imaging apparatus for acquiring a radiographic image includes: a position detector configured to detect a position of an X-ray receiver, in which the X-ray receiver is configured to receive a radiant ray radiated by an X-ray radiator, which radiates a radiant ray, and output an electrical signal in accordance with the received radiant ray; and a display controller configured to display, on a display unit, image data pertaining to the X-ray receiver and image data pertaining to a radiating area of the radiant ray of the X-ray radiator, overlapped with each other based on the position of the X-ray receiver detected by the position detector.

9 Claims, 7 Drawing Sheets

(56) References Cited

U.S. PATENT DOCUMENTS

| | | | |
|---|---|---|---|
| 6,473,489 B2 * | 10/2002 | Bani-Hashemi et al. | 378/63 |
| 6,478,462 B2 * | 11/2002 | Polkus et al. | 378/206 |
| 6,757,355 B1 * | 6/2004 | Siochi | 378/65 |
| 6,890,099 B2 * | 5/2005 | Tanaka et al. | 378/205 |
| 6,893,157 B2 * | 5/2005 | Arakawa | 378/205 |
| 7,490,986 B2 * | 2/2009 | Takekoshi et al. | 378/205 |
| 7,522,701 B2 * | 4/2009 | Jensen et al. | 378/62 |
| 7,555,100 B2 * | 6/2009 | Wang et al. | 378/98.12 |
| 7,572,057 B2 * | 8/2009 | Takekoshi et al. | 378/205 |
| 7,708,462 B2 * | 5/2010 | Fujiwara et al. | 378/207 |
| 7,726,879 B2 * | 6/2010 | Abe et al. | 378/206 |
| 7,742,561 B2 * | 6/2010 | Ueki | 378/63 |
| 7,742,569 B2 * | 6/2010 | Graumann | 378/206 |
| 7,841,772 B2 * | 11/2010 | Nishii et al. | 378/206 |
| 7,916,835 B2 * | 3/2011 | Abe et al. | 378/206 |
| 7,991,114 B2 * | 8/2011 | Okunuki et al. | 378/62 |
| 8,275,187 B2 * | 9/2012 | Oogami | 378/62 |
| 8,622,614 B2 * | 1/2014 | Carmichael et al. | 378/198 |
| 8,678,648 B2 * | 3/2014 | Lalena et al. | 378/198 |
| 8,891,734 B2 * | 11/2014 | Lalena et al. | 378/116 |

* cited by examiner

RADIOGRAPHIC IMAGING APPARATUS, CONTROL METHOD THEREFOR, AND STORAGE MEDIUM HAVING STORED PROGRAM

BACKGROUND OF THE INVENTION

1. Field of the Invention

The present invention relates to a technology of creating radiographic image data by irradiating an object with a radiant ray.

2. Description of the Related Art

In recent years, an X-ray imaging apparatus used such as in a hospital irradiates an object with an X-ray from an X-ray radiator, detects the X-ray that has passed through the object by an X-ray receiver, outputs it as an electrical signal, which is then image-processed, for creating so-called X-ray image data. Therefore, it is necessary that the X-ray radiator and the X-ray receiver be arranged to face each other.

Japanese Patent Application Laid-Open No. 2009-100948 discloses a technique of detecting a radiating region that has been irradiated with an X-ray, detecting the presence/absence of a relative position shift between an X-ray radiator and an X-ray sensor using position information based on the radiating region, and controlling X-ray radiation by the X-ray radiator. Japanese Patent Application Laid-Open No. 2000-135212 discloses a technique of displaying image data acquired by a visible camera overlaid with an external form acquired by a flat surface sensor.

Japanese Patent Application Laid-Open No. H09-66116 discloses a technique of irradiating a body surface of a subject with a light (an index light) as an index for marking an area of the body surface of the subject to be irradiated with a therapeutic radiant ray.

In a mobile X-ray imaging apparatus or the like, which has an X-ray imaging apparatus installed in a movable carriage for performing X-ray imaging at a destination, the X-ray radiator and the X-ray receiver need to face each other at every imaging opportunity. Nevertheless, it is difficult to cause the X-ray radiator and the X-ray receiver to accurately face each other since the X-ray receiver is hidden behind a subject (patient) to be an object, a bed sheet, clothing, and the like.

Using the techniques disclosed in the above-described three patent documents, a user is still unable to check a radiating area of the X-ray radiator and a position of the X-ray receiver simultaneously, whereby it is difficult to cause the X-ray radiator and the X-ray receiver to accurately face each other.

Therefore, an objective of the present invention is to make it easy for a radiating unit and a receiving unit to face each other.

SUMMARY OF THE INVENTION

A radiographic imaging apparatus according to an embodiment of the present invention includes: an X-ray radiator configured to radiate a radiant ray; an imaging unit portion configured to image in substantially the same direction as a direction of radiant ray radiation by the X-ray radiator; a position detector configured to detect a position of an X-ray receiver, in which the X-ray receiver is configured to receive the radiant ray radiated by the X-ray radiator in an imaged area of the imaging portion, and output an electrical signal in accordance with the received radiant ray; and a display controller configured to display, on a display unit, image data pertaining to the X-ray receiver superposed on image data imaged by the imaging portion based on the position of the X-ray receiver detected by the position detector.

Further features of the present invention will become apparent from the following description of exemplary embodiments with reference to the attached drawings.

DESCRIPTION OF THE EMBODIMENTS

Preferred embodiments to which the present invention is applied are described herein in detail with reference to the attached drawings.

Figure 1:
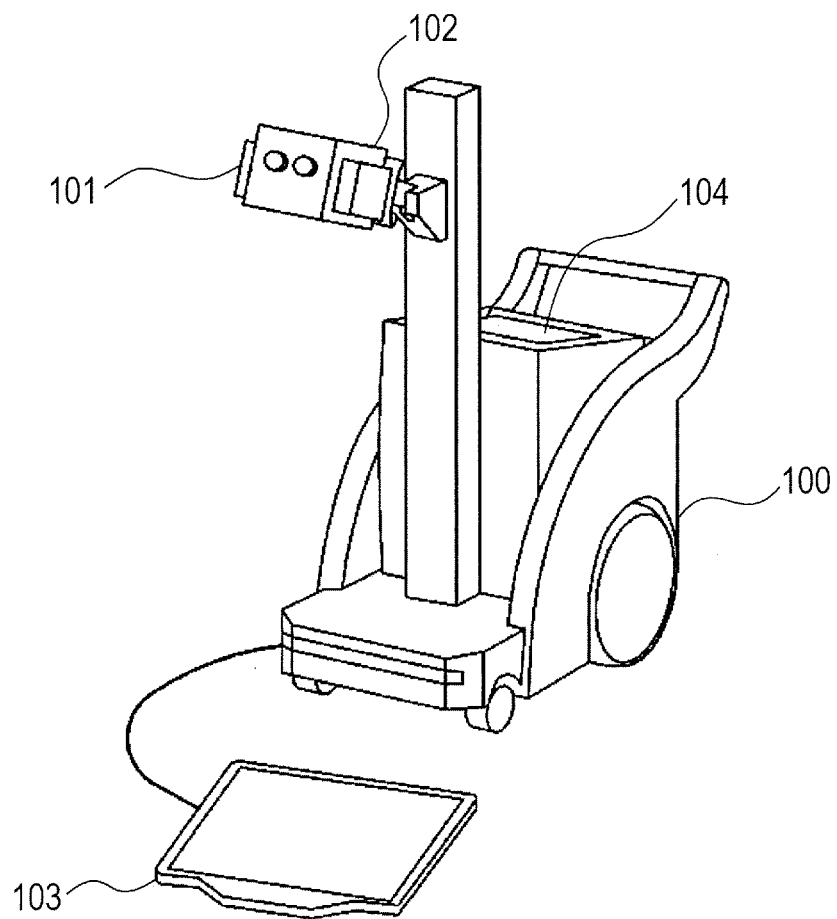
FIG. 1 is a view of an external configuration of an X-ray imaging apparatus according to a first embodiment of the present invention.

First, a first embodiment of the present invention is described herein. FIG. 1 is a view of an external configuration of an X-ray imaging apparatus according to the first embodiment of the present invention. As in FIG. 1, the X-ray imaging apparatus according to this embodiment includes a rounding car 100, an X-ray radiator 101, an imaging portion 102, an X-ray receiver 103, and a display unit 104. The X-ray imaging apparatus is movable by a moving mechanism of the rounding car 100.

Note that the X-ray imaging apparatus according to this embodiment is expected to create radiographic image data by radiating an X-ray, a type of radiant rays, and detecting the X-ray that has passed through the subject. However, a radiant ray applicable to the present invention is not limited to the X-ray but also includes other types of radiant rays such as an α ray, a β ray, or a γ ray. In other words, the X-ray imaging apparatus according to this embodiment is an exemplary radiographic imaging apparatus.

Inside a housing of the rounding car 100, there is provided a controller for controlling the X-ray imaging apparatus. The controller, which is provided with a CPU, a ROM, a RAM, and the like, controls X-ray radiation by the X-ray radiator 101 and image display by the display unit 104, and detects a position of the X-ray receiver 103 relative to the X-ray radiator 101.

The X-ray radiator 101 is provided with a mechanism for generating the X-ray including an X-ray tube, a collimator (for narrowing an X-ray), and the like. The imaging portion 102 is arranged in a position conjugate with the X-ray tube via a half mirror provided inside the X-ray radiator 101, and is configured to image in substantially the same direction as a direction of X-ray radiation. The X-ray receiver 103 is a type of photoelectric sensors, which receives the X-ray radiated by the X-ray radiator 101 and outputs an electrical signal corresponding to the received X-ray. The electrical signal output from the X-ray receiver 103 is input to the controller inside the housing of the rounding car 100.

The display unit 104 includes a common display monitor such as a CRT or a liquid crystal display for displaying image data, a graphical user interface (GUI), and the like on the screen. The X-ray imaging apparatus is also provided with an input device such as a foot pedal, a key board, and a mouse (all of these are not shown) for allowing a user to operate and control the X-ray imaging apparatus.

Figure 2:
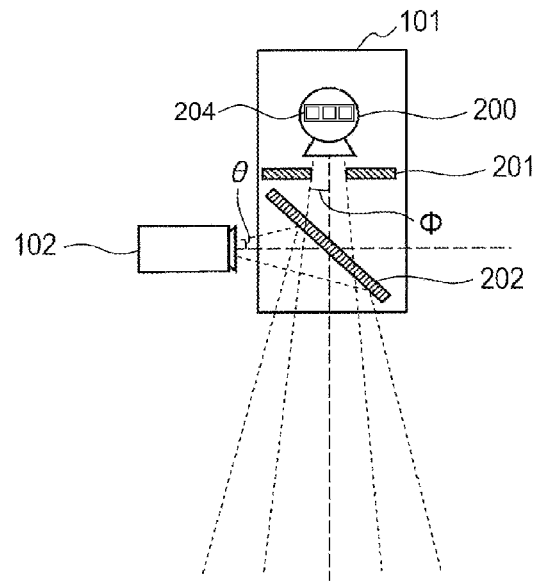
FIG. 2 is a view illustrating a positional relation between an X-ray radiator and an imaging portion.

Next, the positional relation between the X-ray radiator 101 and the imaging portion 102 is described with reference to FIG. 2. As in FIG. 2, the X-ray radiator 101 includes an X-ray tube 200 for generating the X-ray, a collimator 201 for limiting a radiating direction and a radiating region of the X-ray generated in the X-ray tube 200, and a half mirror 202 for passing the X-ray through and reflecting visible rays. The imaging portion 102 is arranged in optically the same position (conjugate position) as the X-ray tube 200, and is capable of imaging in substantially the same direction as the direction of X-ray radiation. Note that the method for the imaging portion 102 to image in substantially the same direction as the direction of X-ray radiation by the X-ray radiator 101 is not limited to this method. For example, a method of arranging the imaging portion 102 and the X-ray radiator 101 very close to each other, or as disclosed in Japanese Patent Application Laid-Open No. 08-84351, a method of acquiring image data having an arbitrary viewpoint and an arbitrary direction among a plurality of the acquired image data and interpolation image data may also be used.

Figure 3:
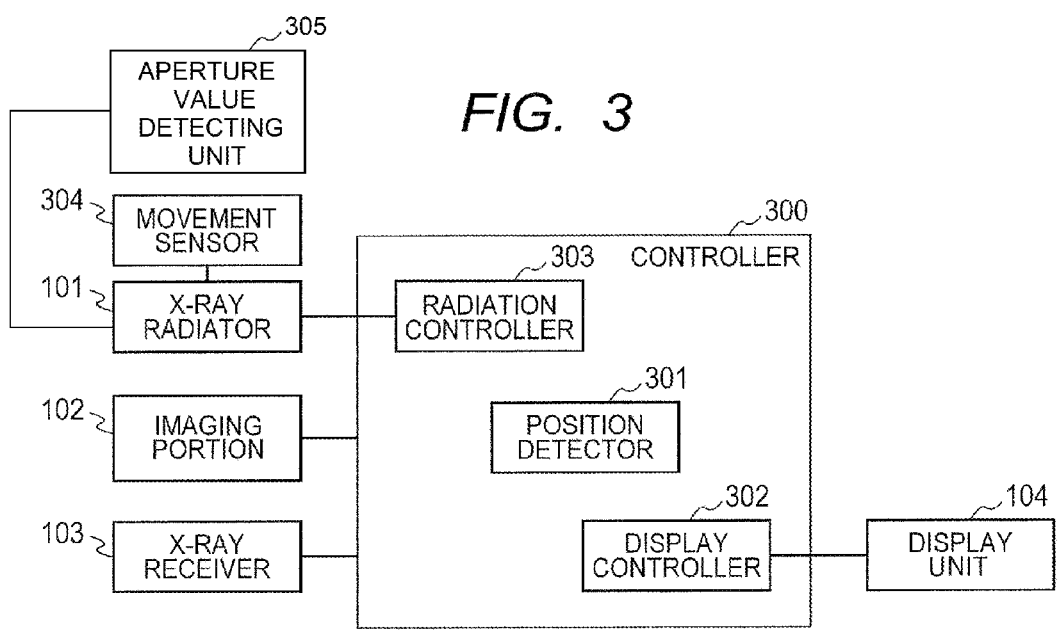
FIG. 3 is a block diagram illustrating a functional configuration of a controller.

Next, a functional configuration of the controller provided inside the housing of the rounding car 100 is described herein. FIG. 3 is a block diagram illustrating the functional configuration of a controller 300. As in FIG. 3, the controller 300 includes a position detector 301, a display controller 302, and a radiation controller 303, as the functional configuration thereof. As described above, the controller 300 includes the CPU, the ROM, and the RAM, as the hardware configuration thereof. The position detector 301, the display controller 302, and the radiation controller 303 are the functional configuration realized by the CPU, which reads necessary data and a program from the ROM, expands them on the RAM, and executes them.

The position detector 301 detects a position of the X-ray receiver 103 relative to the X-ray radiator 101. The display controller 302 creates the so-called X-ray image data based on the electrical signal output from the X-ray receiver 103, and displays the image data on the display unit 104. The display controller 302 creates virtual image data of the X-ray receiver 103 based on the position of the X-ray receiver 103 relative to the X-ray radiator 101 detected by the position detector 301. Then, the display controller 302 combines image data imaged by the imaging portion 102 with the virtual image data of the X-ray receiver 103 and the image data pertaining to the radiating area to be irradiated with the X-ray by the X-ray radiator 101, and displays them on the display unit 104. The radiation controller 303 instructs and controls an imaging start/end (irradiating start/end) and an X-ray radiating pattern of the X-ray radiator 101. A movement sensor 304, provided in a linked manner with the X-ray radiator 101, detects a direction and an amount of movement of the X-ray radiator 101. Various types of sensors are practically available as the movement sensor 304, including a capacitance type and a vibrational gyroscope type. An aperture value detecting unit 305, provided in a linked manner with the X-ray radiator 101, detects an aperture value of the collimator 201.

Figure 4:
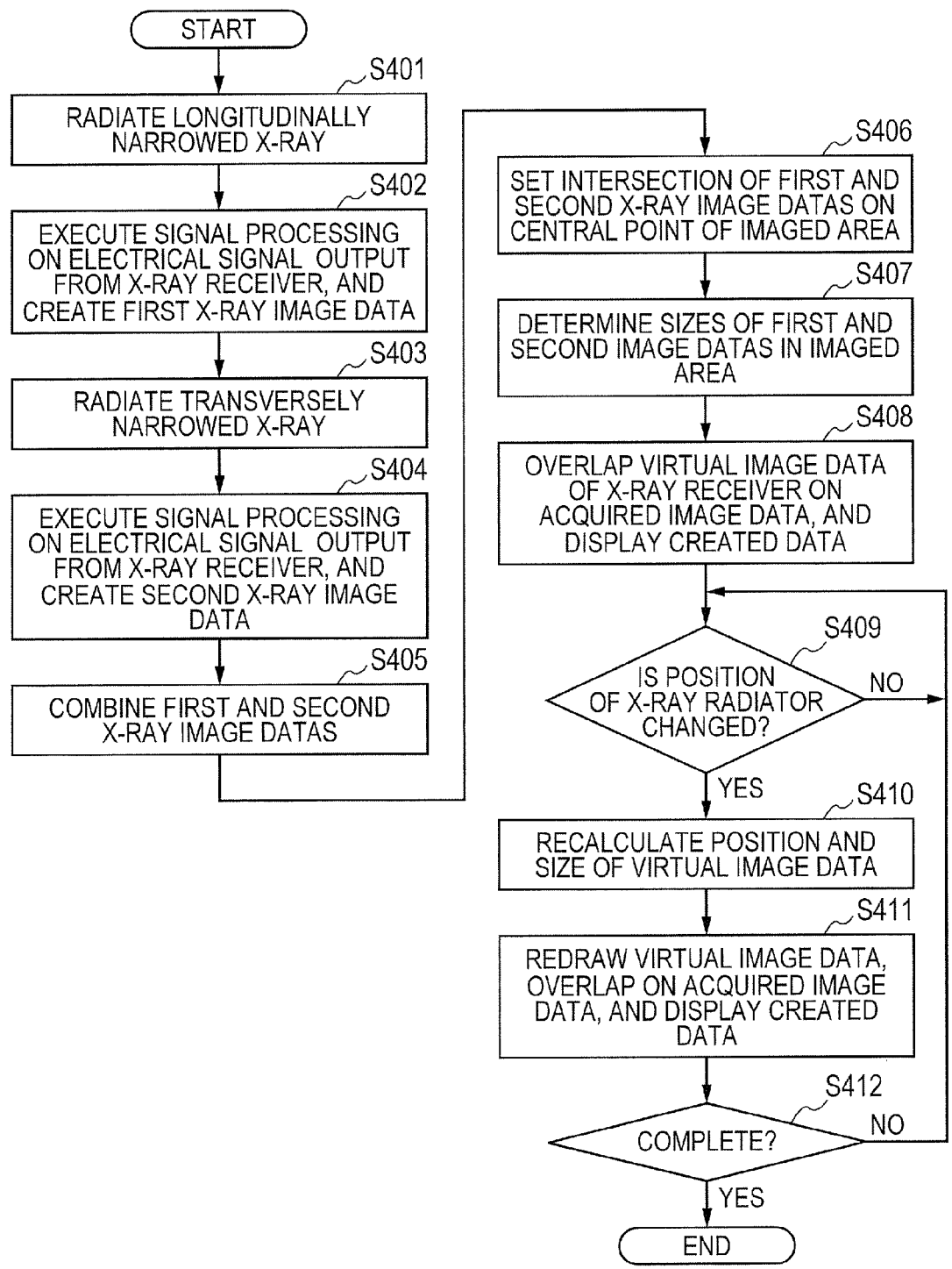
FIG. 4 is a flowchart illustrating processing of the X-ray imaging apparatus according to the first embodiment of the present invention.
Figure 5A:
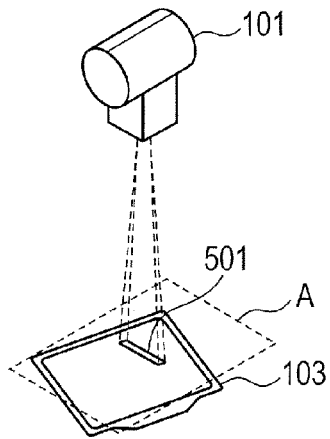
FIGS. 5A, 5B, 5C, 5D, 5E and 5F are views illustrating virtual image data of an X-ray receiver.
Figure 5B:
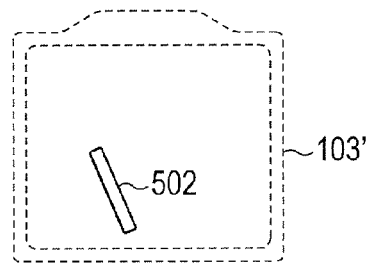

Next, processing of the X-ray imaging apparatus according to the first embodiment of the present invention is described with reference to FIGS. 4 and 5A to 5F. FIG. 4 is a flowchart illustrating the processing of the X-ray imaging apparatus according to the first embodiment of the present invention. FIGS. 5A to 5F are views illustrating the virtual image data of the X-ray receiver 103. Note that FIG. 5A is a view of an imaged area of the imaging portion 102, and FIG. 5B is a view of the virtual image data of the X-ray receiver 103.

In Step S401, as in FIG. 5A, the radiation controller 303 instructs the X-ray radiator 101 to irradiate the X-ray receiver 103 with an X-ray 501, which is longitudinally narrowed by the collimator 201. In Step S402, as in FIG. 5B, the display controller 302 creates first X-ray image data 502 corresponding to the X-ray 501 by performing signal processing on the electrical signal output from the X-ray receiver 103 that has received the X-ray 501. Note that reference numeral 103' denotes a virtual position of the X-ray receiver 103.

Figure 5C:
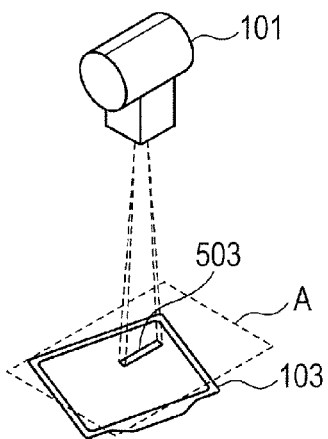
Figure 5D:
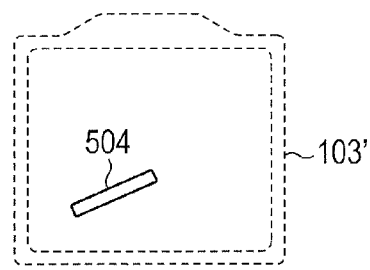

In Step S403, as in FIG. 5C, the radiation controller 303 instructs the X-ray radiator 101 to irradiate the X-ray receiver 103 with an X-ray 503, which is transversely narrowed by the collimator 201. In Step S404, as in FIG. 5D, the display controller 302 creates second X-ray image data 504 corresponding to the X-ray 503, by performing signal processing on the electrical signal output from the X-ray receiver 103 that has received the X-ray 503.

Figure 5E:
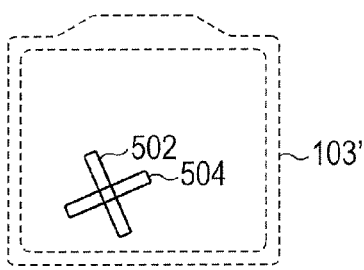

In Step S405, as in FIG. 5E, the display controller 302 combines the first X-ray image data 502 and the second X-ray image data 504 to be orthogonal with each other at each center. In Step S406, the display controller 302 sets an intersection of the first X-ray image data 502 and the second X-ray image data 504 to be on a central point of an imaged area A of the imaging portion 102. This is because the imaging portion 102 images in substantially the same direction as the direction of X-ray radiation by the X-ray radiator 101. In Step S407, the display controller 302 compares an imaging view angle (zoom ratio) of the imaging portion 102 with an aperture value of the collimator 201 to set sizes of the first X-ray image data 502 and the second X-ray image data 504 in the imaged area A.

Figure 5F:
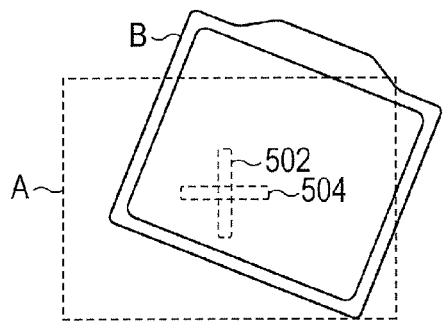

In Step S408, as in FIG. 5F, the display controller 302 calculates a position and size of virtual image data B in the imaged area A based on positions and sizes of the first X-ray image data 502 and the second X-ray image data 504 in the imaged area A. Then, based on the calculated position and size of the virtual image data B in the imaged area A, the display controller 302 superposes the virtual image data B on the image data that has been imaged by the imaging portion 102. Then, the display controller 302 displays the image data superposed with the virtual image data B on the display unit 104.

In Step S409, the radiation controller 303 determines whether or not the position of the X-ray radiator 101 has been changed based on the direction and the amount of movement of the X-ray radiator 101 detected by the movement sensor 304. In the case where the position of the X-ray radiator 101 has been changed, the processing proceeds to Step S410. On the other hand, in the case where the position of the X-ray radiator 101 has not been changed, the processing returns to Step S409, and waits until the position of the X-ray radiator 101 is changed. Note that Step S409 is exemplary processing of the movement sensor 304.

In Step S410, the display controller 302 recalculates the position and size of the virtual image data B in the imaged area A. In Step S411, the display controller 302 redraws the virtual image data B, superposes it on the acquired image data, and displays it on the display unit 104. In Step S412, the display controller 302 determines whether or not a predetermined termination condition such as power-off by a user has been satisfied. In the case where the predetermined termination condition has been satisfied, the processing ends. On the other hand, in the case where the predetermined termination condition has not been satisfied, the processing returns to Step S409.

Note that in the above method, the X-ray radiated for detecting the position of the X-ray receiver 103 may be weak compared to the X-ray radiated for acquiring image data for medical diagnosis, because there is less necessity to consider an image noise and the like. Furthermore, a method of detecting the position of the X-ray receiver 103 in the imaged area A is not limited to the above method. For example, each of the X-ray radiator 101 and the X-ray receiver 103 may receive positioning information transmitted from a global positioning system (GPS) satellite on a satellite radio wave, and may detect an attitude angle by an attitude angle sensor (e.g. a geomagnetic sensor). Based on the positioning information and the attitude angle information, the position detector 301 calculates a position of the X-ray receiver 103 relative to the X-ray radiator 101. There is also a method for the position detector 301 to detect the position of the X-ray receiver 103 in the imaged area A based on the position of the X-ray receiver 103 relative to the X-ray radiator 101 and the imaging view angle (zoom ratio) of the imaging portion 102.

Figure 6A:
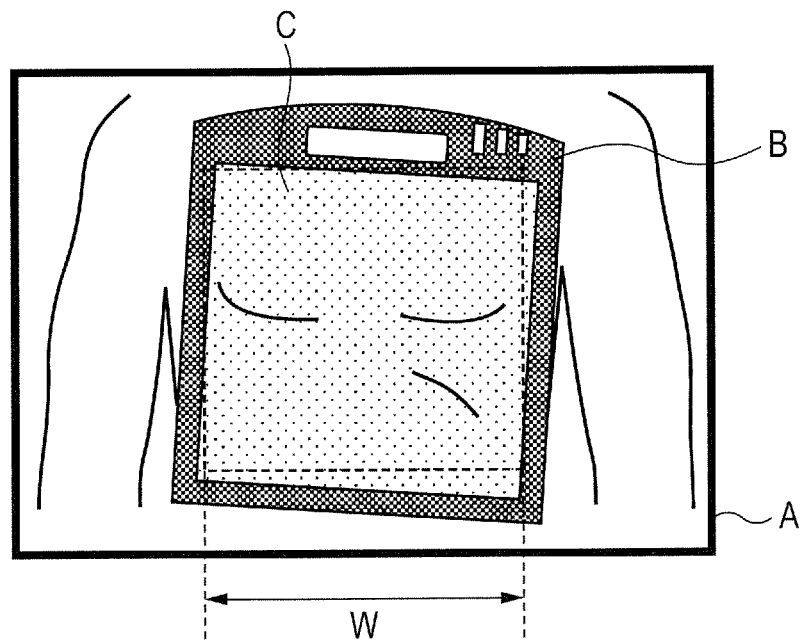
FIGS. 6A and 6B are views illustrating usage of the X-ray imaging apparatus according to the first embodiment of the present invention.
Figure 6B:
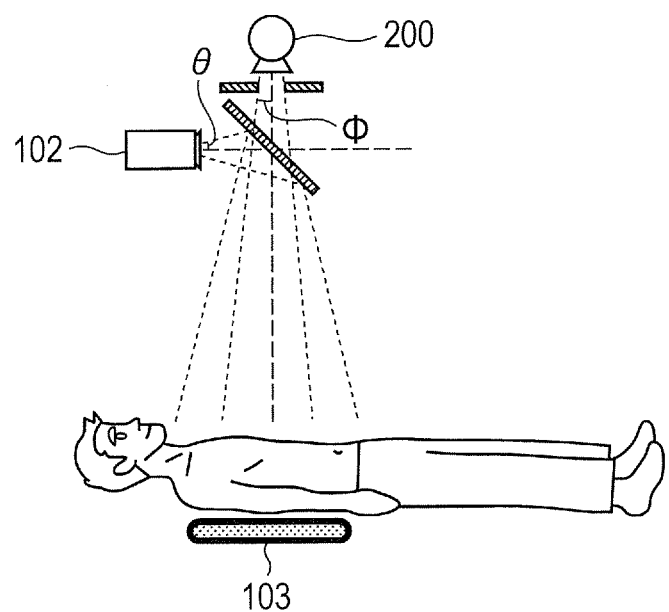

FIGS. 6A and 6B are views illustrating usage of the X-ray imaging apparatus according to this embodiment. As in FIG. 6B, the X-ray imaging apparatus according to this embodiment has the X-ray receiver 103 arranged in the back of the subject, and images in substantially the same direction as the direction of X-ray radiation (subject's chest) by the imaging portion 102 arranged in a position conjugate with the X-ray tube 200 of the X-ray radiator 101. Accordingly, as in FIG. 6A, the virtual image data B of the X-ray receiver 103 and virtual image data C, showing the X-ray radiating area, are superposed on the image data of the imaged area A, and are displayed on the display unit 104. Note that the center of the virtual image data C, showing the X-ray radiating area, corresponds with the center of the imaged area A as in FIG. 6A, since the imaging portion 102 images in substantially the same direction as the direction of X-ray radiation by the X-ray radiator 101.

A method of creating the virtual image data C, showing the X-ray radiating area, is described herein. As in FIG. 6B, the imaging view angle (zoom ratio) of the imaging portion 102 is set to θ, and the radiating angle determined by the aperture value of the collimator 201 is set to Φ. When the imaging view angle (zoom ratio) of the imaging portion 102 in the transverse direction is set to θh, and the radiating angle in the transverse direction determined by the aperture value of the collimator 201 is set to Φh, the ratio of the length w of the X-ray radiating area in the transverse direction to the length of the whole imaged area A in the transverse direction becomes tan Φh/tan θh. Similarly, when the imaging view angle (zoom ratio) of the imaging portion 102 in the longitudinal direction is set to θv, and the radiating angle in the longitudinal direction determined by the aperture value of the collimator 201 is set to Φv, the ratio of the length of the X-ray radiating area in the longitudinal direction to the length of the whole imaged area A in the longitudinal direction becomes tan Φv/tan θv. As above, the X-ray radiating area can be obtained from the imaged area A, whereby the virtual image data C, showing the X-ray radiating area, can be created.

The X-ray imaging apparatus according to this embodiment is capable of displaying, on the display unit 104, the image data of the imaged area A imaged by the imaging portion 102, which is superposed with the virtual image data B of the X-ray receiver 103 and the virtual image data C, showing the X-ray radiating area. Therefore, a user can adjust a position and an angle of the X-ray radiator 101 to face the X-ray receiver 103 by referring to the display unit 104.

Furthermore, when a user changes the aperture value of the collimator 201, in accordance with this, the length of the virtual image data C, showing the X-ray radiating area, is changed at least in either of the transverse direction or the longitudinal direction. Therefore, the user can adjust the aperture value of the collimator 201 while simultaneously checking the size of an object (affected area) in the image data of the imaged area A imaged by the imaging portion 102, and the virtual image data C, showing the X-ray radiating area. Note that the above-described processing of detecting the change in the aperture value of the collimator 201 is exemplary processing of the aperture value detecting unit 305.

Figure 7:
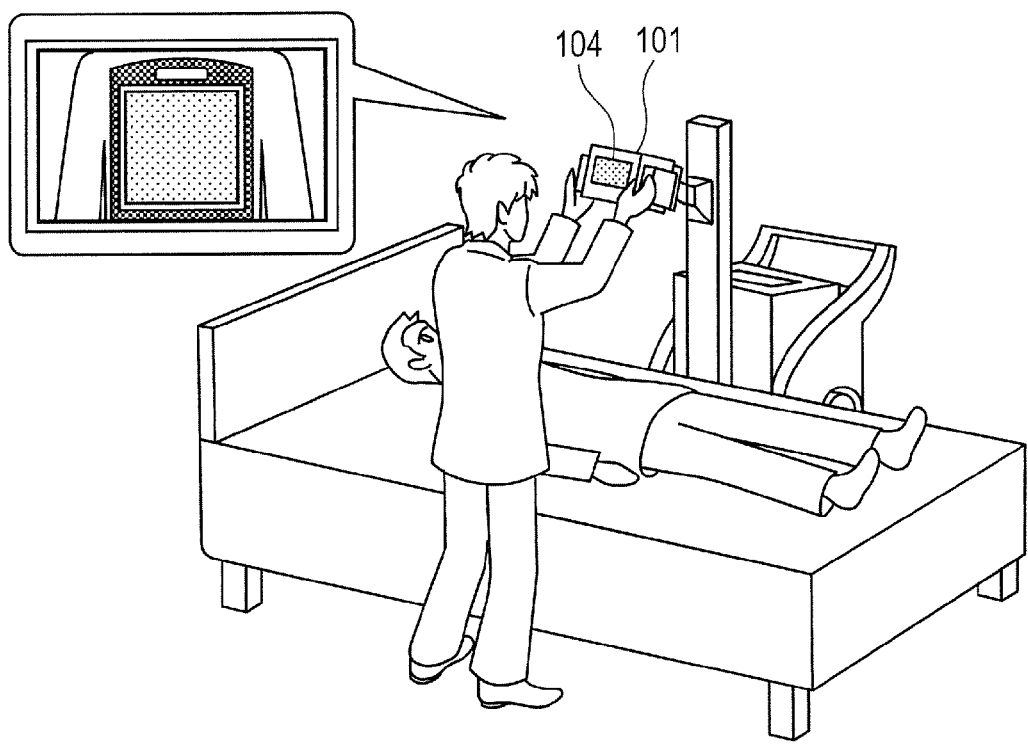
FIG. 7 is a view illustrating usage of an X-ray imaging apparatus according to a second embodiment of the present invention.

Next, a second embodiment of the present invention is described herein. FIG. 7 is a view illustrating usage of an X-ray imaging apparatus according to the second embodiment of the present invention. The X-ray imaging apparatus according to the second embodiment of the present invention includes an X-ray radiator 101 provided with a display unit 104, whereby a user can adjust a position and an angle of the X-ray radiator 101 by referring to the display unit 104. Note that the second embodiment is the same as the first embodiment except that the display unit 104 is provided in the X-ray radiator 101.

Next, a third embodiment of the present invention is described herein. In recent years, there has been known an X-ray radiator using a cold cathode-type multi-electron source as an electron source alternative to the above-described X-ray tube. The X-ray radiator using such a multi-electron source is configured to have a small-sized electron source disposed in a planar state, whereby it may be compactly configured overall. Furthermore, since an X-ray source using the multi-electron source has a plurality of foci, it is capable of radiating the X-ray in a predetermined radiation pattern (for example, in a cross shape) for detecting the position of the X-ray receiver by a single X-ray radiation. An X-ray imaging apparatus according to the third embodiment of the present invention applies an X-ray radiator using the above-described multi-electron source 204, as shown in FIG. 2, as the X-ray radiator 101 in FIG. 1. Any other configuration is the same as that of the X-ray imaging apparatus according to the first embodiment.

Figure 8:
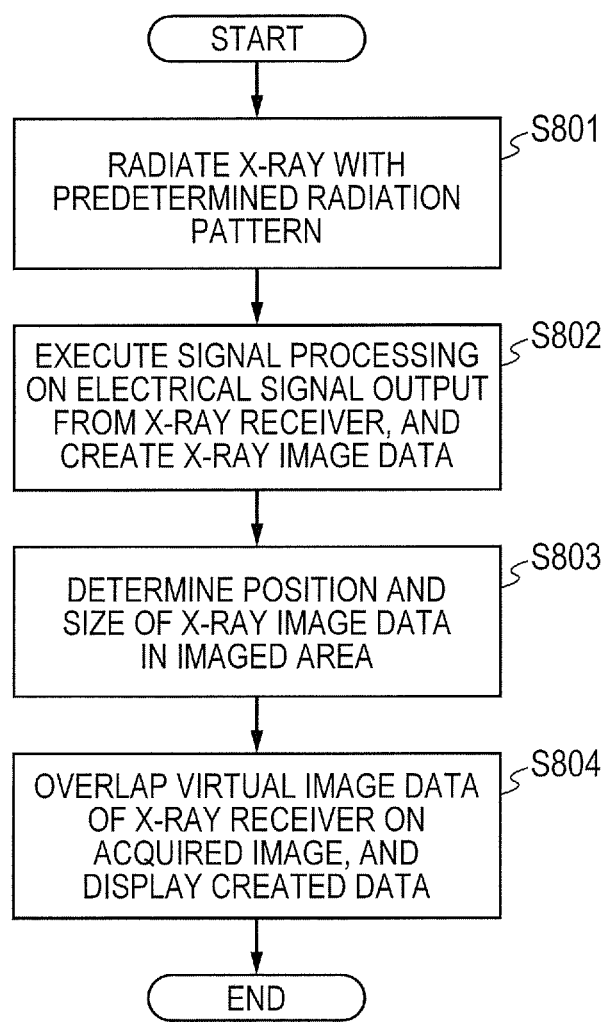
FIG. 8 is a flowchart illustrating processing of an X-ray imaging apparatus according to a third embodiment of the present invention.

FIG. 8 is a flowchart illustrating processing of the X-ray imaging apparatus according to the third embodiment of the present invention. The processing of the X-ray imaging apparatus according to the third embodiment of the present invention is described herein in detail with reference to FIG. 8.

In Step S801, a radiation controller 303 instructs the X-ray radiator 101 to irradiate an X-ray receiver 103 with the X-ray in the predetermined radiation pattern (for example, in the cross shape). In Step S802, a display controller 302 performs signal processing on an electrical signal output from the X-ray receiver 103 that has received the X-ray, and creates X-ray image data. In Step S803, the display controller 302 compares the acquired X-ray image data with the above predetermined radiation pattern to set a position and a size of the X-ray image data in the imaged area A. In Step S804, based on the position and the size of the above X-ray image data, the display controller 302 superposes virtual image data B of the X-ray receiver 103 on the X-ray image data in the imaged area A, and displays them on a display unit 104. Note that Steps S803 and S804 are the same processing as Steps S407 and S408 in FIG. 4.

According to the third embodiment of the present invention, the position of the X-ray receiver 103 can be detected by a single X-ray radiation. Since it is not necessary to change the aperture value for each X-ray radiation, the position of the X-ray receiver 103 can be detected quickly.

Furthermore, the present invention is also realized by executing the following processing. That is the processing to supply software (a program) for realizing functions of the above-described embodiments to a system or an apparatus via a network or a variety of storage media, whereby a computer (or a CPU, an MPU, and the like) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-093983, filed on Apr. 17, 2012, which is hereby incorporated by reference herein in its entirety.

What is claimed is:

1. A radiographic imaging apparatus comprising:
a receiving unit configured to receive a radiant ray radiated by a radiating unit and output an electrical signal in accordance with the received radiant ray;
a detecting unit configured to detect a position of the receiving unit;
an imaging unit configured to image in the same direction as a direction of the radiant ray radiated by the radiating unit to obtain image data;
a displaying unit; and
a display control unit configured to create virtual image data showing a radiating area and display, on the displaying unit, virtual image data pertaining to the position of the receiving unit detected by the detecting unit, the virtual image data pertaining to the radiating area associated with the radiating unit, and image data imaged by the imaging unit, overlapped with each other.

2. The radiographic imaging apparatus according to claim 1, further comprising:
a position detecting unit configured to detect a change in the position of the radiating unit,
wherein the detecting unit redetects the position of the receiving unit in an imaged area of the imaging unit when the change in the position of the radiating unit is detected by the position detecting unit.

3. The radiographic imaging apparatus according to claim 1, further comprising:
an aperture value detecting unit configured to detect an aperture value of a collimator of the radiating unit,
wherein the display control unit changes the virtual image data pertaining to the radiating area associated with the radiating unit according to the aperture value of the collimator detected by the aperture value detecting unit.

4. The radiographic imaging apparatus according to claim 1, further comprising the radiating unit that radiates the radiant ray,
wherein the displaying unit is provided in the radiating unit.

5. The radiographic imaging apparatus according to claim 4, wherein the radiating unit includes a multi-electron source having a plurality of foci.

6. A method for controlling a radiographic imaging apparatus for acquiring a radiographic image, comprising:
detecting a position of a receiving unit, wherein the receiving unit is configured to receive a radiant ray radiated by a radiating unit and output an electrical signal in accordance with the received radiant ray;
imaging, by an imaging unit, in the same direction as a direction of the radiant ray radiated by the radiating unit to obtain image data;
creating virtual image data showing a radiating area; and
displaying, on a displaying unit, virtual image data pertaining to the position of the receiving unit detected by a detecting unit, virtual image data showing the radiating area, and image data imaged by the imaging unit, overlapped with each other.

7. A non-transitory storage medium having stored a computer program for allowing a computer to execute a control method for a radiographic imaging apparatus for acquiring a radiographic image, the control method comprising:
detecting a position of a receiving unit, wherein the receiving unit is configured to receive a radiant ray radiated by a radiating unit and output an electrical signal in accordance with the received radiant ray;
imaging, by an imaging unit, in the same direction as a direction of the radiant ray radiated by the radiating unit to obtain image data;
creating a virtual image data showing a radiating area; and
displaying, on a displaying unit, virtual image data pertaining to the position of the receiving unit detected by a detecting unit, virtual image data showing the radiating area, and image data imaged by the imaging unit, overlapped with each other.

8. A radiographic imaging apparatus comprising:
a detecting unit configured to detect a position of a receiving unit, wherein the receiving unit is configured to receive a radiant ray radiated by a radiating unit and output an electrical signal in accordance with the received radiant ray;
a display control unit configured to display, on a displaying unit, virtual image data pertaining to the position of the receiving unit detected by the detecting unit and virtual image data pertaining to a radiating area associated with the radiating unit, overlapped with each other; and
a position detecting unit configured to detect a change in a position of the radiating unit,
wherein the detecting unit redetects the position of the receiving unit in an imaged area of an imaging unit when the change in the position of the radiating unit is detected by the position detecting unit.

9. A radiographic imaging apparatus comprising:
a detecting unit configured to detect a position of a receiving unit, wherein the receiving unit is configured to receive a radiant ray radiated by a radiating unit and output an electrical signal in accordance with the received radiant ray;
a display control unit configured to display, on a displaying unit, virtual image data pertaining to the position of the receiving unit detected by the detecting unit and virtual image data pertaining to a radiating area associated with the radiating unit, overlapped with each other; and
an aperture value detecting unit configured to detect an aperture value of a collimator of the radiating unit,
wherein the display control unit changes the image data pertaining to the radiating area of the radiating unit according to the aperture value of the collimator detected by the aperture value detecting unit.

* * * * *